United States Patent [19]
Anbar

[11] Patent Number: 5,961,466
[45] Date of Patent: Oct. 5, 1999

[54] METHOD OF DETECTION OF CANCEROUS LESIONS BY THEIR EFFECT ON THE SPATIAL DISTRIBUTION OF MODULATION OF TEMPERATURE AND HOMOGENEITY OF TISSUE

[75] Inventor: Michael Anbar, Williamsville, N.Y.

[73] Assignee: Omnicorder Technologies, Inc., Stoneybrook, N.Y.

[21] Appl. No.: 09/085,627

[22] Filed: May 27, 1998

Related U.S. Application Data

[63] Continuation-in-part of application No. 08/368,161, Jan. 3, 1995, Pat. No. 5,810,010.

[51] Int. Cl.$^6$ .................................................. A61B 6/00
[52] U.S. Cl. ........................ 600/474; 600/475; 600/549
[58] Field of Search .................................. 600/474, 473, 600/475, 549, 310

[56] References Cited

U.S. PATENT DOCUMENTS

| | | | |
|---|---|---|---|
| 4,366,381 | 12/1982 | Fischer et al. | 600/474 |
| 4,428,382 | 1/1984 | Walsall et al. | 600/549 |
| 4,809,701 | 3/1989 | Le Bihan et al. | 128/653 |
| 5,205,293 | 4/1993 | Ito et al. | 128/691 |
| 5,207,222 | 5/1993 | Koizumi et al. | 128/653.2 |
| 5,207,227 | 5/1993 | Powers | 128/691 |
| 5,233,994 | 8/1993 | Shmulewitz | 128/661.08 |
| 5,445,157 | 8/1995 | Adachi et al. | 128/664 |
| 5,588,437 | 12/1996 | Byrne et al. | 128/691 |
| 5,678,555 | 10/1997 | O'Connell | 600/473 |
| 5,771,261 | 6/1998 | Anbar | 600/474 |
| 5,845,639 | 12/1998 | Hochman et al. | 600/473 |

OTHER PUBLICATIONS

Cancer Letters 84 (1994) Michael Anbar—Hyperthermia of the cancerous breast: analysis of mechanism; pp. 23–29.

Journal of Pain and Symptom Management; Special Article—Role of Nitric Oxide in the Physiopathology of Pain; Michael Anbar and Barton M. Gratt; pp. 225–254.

Fast Dynamic Area Telethermometry (DAT) of the Human Forearm With A Ga/As Quantum Well Infrared Focal Plane Array Camera; Michael Anbar, M.W. Grenn, M.T. Marion, L. Milescu and K. Zamani; pp. 105–118.

Manifestation of Neurological Abnormalities Through Frequency Analysis of Skin Temperature Regulation; Michael Anbar, and James C. Montoro, Kyu Ha Lee and Sean D'Arcy; 1991; pp. 234–241.

Biomedical Termology; 13; Local "Micro" Variance In Temperature Distribution Evaluated By Digital Thermography; Michael Anbar and Robert F. Haverley; pp. 173–187, 1994.

Simultaneous Acquisition of Thermal and Visible Images in A Scanning Infrared Camera; Shahram Hejazi, Omid A. Moghadam, Robert A. Spangler and Michael Anbar; SPIE vol. 2020 Infrard Technology XIX, pp. 510–516.

*Primary Examiner*—Brian L. Casler
*Attorney, Agent, or Firm*—Hodgson, Russ, Andrews, Woods & Goodyear LLP

[57] ABSTRACT

A method for measuring the periodicity of changes in blood perfusion over large regions of skin so as to identify a locally impaired neuronal control, thereby providing a quick and inexpensive screening test for relatively shallow neoplastic lesions, such as breast cancer, is described. The present method is predicated on infrared imaging of the skin to detect changes in the spectral structure and spatial distribution of thermoregulatory frequencies (TRFs) over different areas of the skin.

32 Claims, No Drawings

METHOD OF DETECTION OF CANCEROUS LESIONS BY THEIR EFFECT ON THE SPATIAL DISTRIBUTION OF MODULATION OF TEMPERATURE AND HOMOGENEITY OF TISSUE

CROSS-REFERENCE TO RELATED APPLICATION

The present application is a continuation-in-part of application Ser. No. 08/368,161, filed Jan. 3, 1995 now U.S. Pat. No. 5,810,013.

BACKGROUND OF THE INVENTION

The present invention relates generally to cancer detection and, more particularly, to a cancer detection method involving the measurement, recording and analysis of temporal periodic perfusion changes associated with dysfunction of neuronal control of the vasculature surrounding cancerous lesions. While the present invention has application to cancer detection throughout the human body, it is particularly applicable to a breast cancer screening test involving the measurement of temporal changes in perfusion over large areas of the breasts to identify cancer. Specifically, cancer detection is derived from a time series of infrared images of an area of interest of a human breast. The infrared images relate to the temporal periodic perfusion changes and are converted by a computer to time series average temperature and standard deviation of each of a plurality of subareas. The data is then analyzed to identify clusters having abnormal temperature dependent frequencies indicative of cancer.

SUMMARY OF THE INVENTION

Thermoregulatory frequencies of the processes that control skin temperature over different areas of the body are derived from the periodic changes in temperature distribution over those skin areas. As shown by Dr. Anbar in the European J Thermology 7:105–118, 1997, under conditions of hyperperfusion, the homogeneity of the skin temperature distribution reaches a maximum and the amplitude of its temporal modulation is at a minimum. In other words, periodic changes in the spatial homogeneity of skin temperature (HST) are dictated by the processes that control the saturation of the cutaneous capillary bed in a particular area of the skin. Accordingly, skin temperature and HST are independent physiological hemodynamic parameters that are determined by the structure of the cutaneous vasculature and by its heat dissipatory activity. However, unlike average temperature, HST is affected mainly by the behavior of the cutaneous capillaries and to a much lesser extent by the blood flow in subcutaneous vessels. As perfusion is enhanced, more capillaries are recruited as blood conduits and HST increases. The neuronal control of HST is, therefore, different from that of skin temperature. Consequently, the spatial distribution of changes in skin temperature and homogeneity, HST, of tissue derived from a time series of infrared images of a skin area according to the present invention is more informative than a classical thermogram. HST is the reciprocal of the spatial coefficient of variation of temperature in small ("micro") areas of skin (<100 mm$^2$): HST=average temperature divided by the standard deviation of the average temperature (HST is a dimensionless parameter). The concept of HST has been fully described by Dr. Michael Anbar in Biomedical Thermology, 13:173–187, 1994.

These and other objects of the present invention will become increasingly more apparent to those skilled in the art by reference to the following description.

DETAILED DESCRIPTION OF THE PREFERRED EMBODIMENTS

Although skin temperature may vary over a wide range, depending upon the environment and on the level of metabolic activity, it is regulated under normal conditions. This regulation may be occasionally less stringent, like during sleep but even then, some skin regulation is retained. In the human body, skin temperature maintenance is due, in substantial part to neuronal thermoregulation of vasoconstriction and vasodilation of the vasculature, thereby causing a characteristic modulation of blood perfusion, unless the neuronal thermoregulation is inhibited or taken over by a non-neuronal thermoregulatory control, such as nitric oxide (NO). Modulation of skin temperature is on the order of 10 to 50 millidegrees Kelvin.

NO has been recognized as an ubiquitous vasodilatory chemical messenger. Its main role appears to be synchronization of intercellular and inter organ functions, because it diffuses freely in the interstitial space. This has been discussed extensively by Dr. Anbar in J. Pain Symptom Management 14:225–254, 1997. Under certain conditions, such as in breast cancer, autocatalytic production of NO may occur, which results in oscillatory vasodilation, independent of and substantially different from the temperature oscillations of perfusion caused by the neuronal thermoregulatory system. NO can, therefore, inhibit autonomic vasoconstrictive control in substantial regions of the microvasculature and cause regional hyperperfusion. Subcutaneous and cutaneous hyperperfusion are manifested as hyperthermia of the overlying skin.

Thus, cancer associated breast hyperthermia results from impaired neuronal thermoregulation caused by excessive production of NO by breast cancer cells and in macrophages that react to the neoplastic tissue. The latter activity is an expression of the immune response because NO generated by macrophages is a major factor in killing of microorganisms or of mammalian cells recognized as alien. The mechanism for this activity is described fully in a 1994 publication of Dr. Michael Anbar, Cancer Letters 84:23–29, 1994. The rate of production of NO is further enhanced by the presence of ferritin, the level of which is significantly elevated in breast cancerous tissue. Fe$^{2+}$ released from ferritin is used to produce more NO synthase (NOS), an iron carrying enzyme which produces NO from arginine, and thus results in a further increase in the rate of production of NO. Furthermore, NO has been shown to release Fe$^{2+}$ from ferritin by forming an NO-ferritin complex which consequently results in an autocatalytic production of NO. Fe$^{2+}$ also eliminates superoxide radicals (HO$_2$) which are normally the major scavengers of NO. Elimination of HO$_2$ maintains the local high level of NO, and hyperperfusion of the tissues surrounding the cancerous lesion. The ferritin dependent enhancement of NO production seems to be specific to neoplastic cells and is less likely to occur in other inflammatory situations, including those induced by microorganisms.

Therefore, the frequencies of temperature and HST oscillations observed over a cancerous breast differ substantially from those observed over a non-cancerous (normal) breast. The oscillations over a normal breast are caused by the neuronal thermoregulatory processes, which follow several characteristic bands of frequencies. The cancerous area of the breast, on the other hand, which loses its neuronal thermoregulatory control due to the over-production of NO, is characterized by the disappearance of the neuronal oscillations and the appearance of oscillations due to the autocatalysis of NO production, with their typical frequency bands. The latter autocatalytic processes, controlled by the temporary local depletion of one of the precursors of NO, are utterly different in nature from the neurological feedback processes manifested in the neuronal frequency bands. Consequently, the disappearance of neuronal frequencies over substantial parts of the cancerous breast is sufficient to identify pathology. Furthermore, the appearance of the autocatalytic frequencies characteristic of NO over-production is, by itself, sufficient to identify pathology. The substitution of one set of frequency bands by the other is an even more strict criterion of pathology in a human breast. Hemodynamic modulation is generally in the range of 0.8 to 2 Hz, whereas modulation by the autonomic nervous system ranges generally between 10 and 700 mHz.

It is the detection of these frequencies, whether neuronal or non-neuronal, which is the basis of the detection methods of the present invention. Specifically, under conditions of extravascular NO overproduction and its consequent hyperperfusion, skin temperature and the homogeneity of skin temperature, HST, reach values that oscillate at frequencies dependent on the modulated autocatalytic rate of NO production. The frequency bands of the modulation of temperature and HST are, according to the present detection methods, independent criteria of pathology.

It should be understood that while the present detection methods are described herein with respect to a human breast, it is not intended to be so limited. Detection of cancerous lesions in the hands, arms, chest, legs, buttocks, back and literally any other body part is possible with the present methods.

Thus, the screening techniques of the present invention use the spatial distribution of the characteristic oscillations or modulations in the temporal behavior of blood perfusion caused by enhanced NO production by cancerous cells and in macrophages and amplified by ferritin to detect an immune response induced by neoplastic disease. The temperature oscillation of blood perfusion associated with the autocatalytic production of NO, as well as the diminution or disappearance of the neuronal thermoregulatory frequencies, TRFs, are used as the diagnostic parameters. The neuronal and autocatalytic oscillations are measured by fast Fourier transform (FFT) analysis, an analysis method well known in the art, of the temporal behavior of breast perfusion (manifested in the temporal behavior of breast temperature and of HST). The TRFs of HST are, therefore, additional independent diagnostic parameters.

Accordingly, the present invention provides for the accumulation of hundreds of sequential thermal images that are then subjected to FFT to extract the frequencies and amplitudes of periodic changes at each pixel of the image. To measure the spatial distribution of modulation of temperature and HST, an infrared camera is positioned to provide infrared flux images of a part of the human body, for example a human breast. A preferred camera is equipped with a 256×256 focal plane array (FPA) GaAs quantum-well infrared photodetector (QWIP). Such a camera can record modulation of skin temperature and its homogeneity with a precision greater than ±1 millidegrees C, i.e., less than 1/10 of physiological modulation of temperature and of homogeneity of human skin. Another camera that is useful with the present invention is a HgCdTi infrared photodetector.

While successful results can be achieved by analyzing the temporal behavior of at least 128 thermal images, it is most preferred to measure 1024 consecutive thermal images over a period of 10 to 60 seconds. The infrared images are transmitted to a CPU having an analog/digital converter which processes the recorded infrared flux information and outputs digital infrared flux data.

To determine whether the breast is normal or cancerous, the CPU factors the digital data to equivalent temperature readings for a designated spot subarea or group of spots of the breast (each spot subarea corresponds to about 25 to 100 $mm^2$ of skin based on a 256×256 pixel field, as will be described hereinafter), which are later to be analyzed for the presence of lesions. A spot is typically about four to sixteen pixels and can have the shape of a circle, square or other shapes. The temperature values of the pixels in each subarea of the image are averaged. The variance of the average temperature is used to calculate the HST of each subarea. The accumulated images are then analyzed by FFT to extract the corresponding frequencies of the average temperature and standard deviation of average temperature. The FFT yields the frequency spectra of each pixel together with the relative amplitude of each TRF. The software then tabulates, or displays as color-coded bitmaps, the spatial distribution of the TRFs within a given range of relative amplitudes over the image. The same procedure is followed with the HST data.

When TRFs in a cluster of subareas are displayed with amplitudes above a given threshold, a subset of characteristic neuronal frequencies over areas of breasts free from cancer-enhanced immune response is identified. A cluster is defined as at least six congruent subareas of four to sixteen pixels per subarea. Such TRFs are significantly attenuated or completely absent in areas overlying breasts with neoplastic lesions. The latter areas are characterized by non-neuronal thermoregulatory behavior which manifest substantially different TRFs caused by the autocatalytic production of NO. Also the latter areas are, therefore, characterized by aberrant modulation of blood perfusion and aberrant temperature oscillations. A hard copy in the form of a colored bitmap of the imaged skin area is then generated to allow an expert to anatomically identify the location of the aberrant area, or areas.

The computer algorithms that facilitate this computation are as follows:

A. Use of temperature values of individual pixels and the computation of TRFs.
1. The computerized camera takes an image of the infrared flux (256×256 pixels) of an area of interest of the skin, such as of a human breast, and converts it into a digital thermal image where each pixel has a certain temperature value. This process is repeated, preferably thirty times a second until 1024 thermal images have been accumulated and stored in the computer.
2. The infrared image is subdivided into subareas of 4 to 16 pixels, each subarea corresponding to about 25 to 100 square millimeters of skin, depending on the optics of the camera and the geometry of the measurement. For example, in a 256×256 pixel field, each pixel represents about 2.4 $mm^2$. Higher resolution camera will have greater skin area detail. The computer then converts each infrared image into a digital thermal image where each pixel has a certain temperature value.
3. The computer calculates the average temperature and the temperature standard deviation of each of the subareas in each of the 1024 images. The average temperature values of each subarea constitutes a single time series that is then subjected to FFT analysis to extract the contributing frequencies of each image of the series and their relative amplitudes. The computer stores the resulting FFT spectrum for the calculated subarea related to the subdivided area of the image. The computer repeats the same procedure for each of the subareas of the image of the skin. Additionally, or in the alternative, the temperature standard deviation value of each subarea can be used to calculate a time series that is subjected to FFT analysis to extract the contributing frequencies of each image of the series and their relative amplitudes.

4. The computer selects the FFT spectra of each of the subareas and displays colored bitmaps of the relative amplitudes derived from the FFT analysis in any exhibited range of frequencies to thereby identify clusters of subareas having frequencies with abnormal amplitudes.

5. If procedure #4 does not identify definitely aberrant clusters, the computer determines that the test is negative for cancer and the patient is normal. A message to this effect is then output by the computer. Otherwise, the computer proceeds with procedure #6.

6. The computer examines all the pixels in the aberrant clusters identified in procedure #4 to identify frequencies with amplitudes that are characteristic of cancer, i.e., at least six congruent subareas wherein a spatial distribution of the amplitude value in the congruent subareas is less than about 10%, and preferably less than about 20%, or more than 100% of the average amplitudes of the temperature values of all of the surrounding subareas.

7. If procedure #4 identifies a definitely aberrant cluster, while procedure #6 turns out negative, the computer prints out a color image of the breast. If procedure #6 yield a confirmation, the computer prints out another color image with the aberrant clusters.

B. Use of HST values and the computation of HST TRFs.

1. The computerized camera takes on image of the infrared flux (256×256 pixels) of an area of interest of the skin, such as a human breast, and converts it into a thermal image where each pixel has a certain temperature value. This process is respected, preferably thirty times a second until 1024 thermal images have been accumulated and stored in the computer.

2. The infrared image is subdivided into subareas of 4 to 16 pixels, each subarea corresponding to about 25 to 100 square millimeters of skin, based on the 256×256 optics resolution of the camera. The computer then converts each infrared image into a digital thermal image where each pixel has a certain temperature value.

3. The computer calculates the average temperature (AVT) value and temperature standard deviation (SD) of each subarea. The computer then calculates the HST value for each subarea: HST=AVT/SD. The HST values are analyzed by FFT to extract the contributing frequency of each subarea to yield HST TRFs, and the relative amplitude of each frequency.

4. The computer selects the FFT spectra of each of the subareas and displays colored bitmaps of the relative amplitude derived from the FFT analysis in any exhibited range of frequencies to thereby identify clusters of subareas with frequencies having abnormal amplitudes.

5. If procedure #4 does not identify definitely aberrant clusters, the computer determines that the test is negative for cancer and the patient is normal. A message to this effect is then output by the computer. Otherwise, the computer proceeds with procedure #6.

6. The computer examines all the subareas in the aberrant clusters identified in procedure #4 to identify frequencies that are characteristic of cancer, i.e., at least six congruent subareas wherein a spatial distribution of the amplitude value in the congruent subareas is less than about 10%, and preferably less than about 20%, or more than 100% of the amplitudes of the HST values of all of the surrounding subareas.

7. If procedure #4 identifies a definitely aberrant cluster, while procedure #6 turns out negative, the computer prints out a color image of the breast. If procedure #6 yields a confirmation, the computer prints out another color image with the aberrant clusters.

8. A match between the findings of procedure A and B increases the diagnostic certainty of the detection method of the present invention.

According to a further aspect of the present invention, the difference between normal and cancerous breasts is accentuated by a thermal challenge (cooling or warming) of the breasts. Such a thermal challenge affects only the neuronal thermoregulatory system and therefore affects only TRFs in areas that are not vasodilated by excessive extravascular NO production. The computer is programmed to look for the frequency bands of the neuronal and the NO controlled TRFs in every subset of pixels (e.g., 4 to 16 pixels) of the FFT processed image. If the computer does not find any clusters with neuronal TRFs having exceptionally low amplitude (except in the periphery of the image which does not depict skin), and no clusters are found to have the NO controlled autocatalytic TRFs with a significant amplitude, the findings of the test are declared as negative (i.e., normal). This finding is then confirmed by computing and analyzing the HST TRFS. If the computer finds certain clusters with exceptionally low neuronal TRFs and especially if those clusters exhibit the NO controlled autocatalytic TRFS, the test findings are classified as pathological. This finding is then confirmed by analyzing the HST data, as described for the uncooled or unwarmed breast. Cooling or warming of the breasts (by a mild flow of forced air) attains maximal sensitivity and specificity. Such additional testing is administered as a confirmatory test only to patients who show a positive result on the uncooled test.

Although the invention has been described in detail for the purpose of illustration, it is to be understood that such detail is solely for that purpose and that variations can be made therein by those skilled in the art without departing from the spirit and scope of the invention except as it may be limited by the claims.

What is claimed is:

1. A method of detecting cancerous tissue, comprising the steps of:

a) recording a plurality of infrared images of a predetermined area of skin;

b) converting each of the plurality of infrared images into corresponding thermal images;

c) subdividing the predetermined area of skin into a plurality of subareas;

d) calculating an average temperature value for the plurality of thermal images of a selected one of the subareas, wherein the average temperature value for the selected subarea constitutes a time series for that subarea;

e) repeating the procedure of steps a) to d) on the remaining subareas of the predetermined area of the skin; and f) analyzing the average temperature value of the time series of each of the subareas, wherein when a spatial distribution of the average temperature value of a cluster comprising at least six congruent subareas is less than about 20% or more than 100% of the average temperature of the plurality of subareas, that cluster is determined to be cancerous.

2. The method of claim 1 including analyzing the average temperature value of each of the plurality of subareas to determine a contributing frequency of each average temperature value and displaying a presentation of the relative amplitude value of each frequency of the subareas, wherein when a spatial distribution of the amplitude of a given frequency of the cluster is less than about 25% or more than 100% of the average amplitude value of that frequency of the plurality of subareas, that cluster is determined to be cancerous.

3. The method of claim 1 wherein when the spatial distribution of the average temperature amplitude of the cluster is less than about 10% of the average amplitude of the plurality of subareas, that cluster is determined to be cancerous.

4. The method of claim 1 wherein the infrared images are converted to corresponding digital thermal images.

5. The method of claim 1 including providing the infrared image of a field of 256×256 pixels.

6. The method of claim 1 including recording about 128 to 1024 thermal images.

7. The method of claim 6 wherein the thermal images are recorded consecutively.

8. The method of claim 6 including recording the thermal images in a period of about 10 to 60 seconds.

9. The method of claim 1 including subdividing the predetermined area of skin into the plurality of subareas of about 24 to 100 square millimeters of skin based on a 256×256 pixel field.

10. The method of claim 1 including subdividing the predetermined area of skin into a plurality of subareas of about 4 to 16 pixels.

11. The method of claim 1 including analyzing the computed average temperature value of the selected subarea using a fast Fourier transform analysis.

12. The method of claim 1 including determining that the predetermined area of skin is of cancerous tissue.

13. The method of claim 1 including determining that the predetermined area of skin is of non-cancerous tissue.

14. The method of claim 1 including determining that the predetermined area of skin includes both non-cancerous tissue and cancerous tissue.

15. The method of claim 1 including recording the infrared images using either a HgCdTi or a GaAs quantum-well infrared photodetector.

16. The method of claim 1 including providing the presentation as a color-coded bitmap.

17. The method of claim 1 including subjecting the predetermined are of skin to either a cooling or warming air flow.

18. The method of claim 1 wherein the predetermined area of skin is a human breast.

19. A method of detecting cancerous tissue, comprising the steps of:

a) recording a plurality of infrared images of a predetermined area of skin;

b) converting each of the plurality of infrared images into corresponding thermal images;

c) subdividing the predetermined area of skin into a plurality of subareas;

d) calculating an average temperature value and a temperature standard deviation for the plurality of thermal images of each of the subareas;

e) dividing the average temperature by the standard deviation of each of the subareas to derive a homogeneity of skin temperature (HST) value for each subarea, wherein the HST value for each subarea constitutes a time series for that subarea; and f) analyzing the HST value of the time series of each of the subareas, wherein when a spatial distribution of the HST value of a cluster comprising at least six congruent subareas is less than about 20% or more than 100% of the average HST value of the plurality of subareas, that cluster is determined to be cancerous.

20. The method of claim 19 including analyzing the HST value of each of the plurality of subareas to determine a contributing frequency of each HST value and displaying a presentation of the relative amplitude value of each frequency of the plurality of subareas, wherein when a spatial distribution of the amplitude of a given frequency of the cluster is less than about 20% or more than 100% of the average HST value of the plurality of subareas, that cluster is determined to be cancerous.

21. The method of claim 19 wherein the infrared images are converted to corresponding digital thermal images.

22. The method of claim 19 including providing the infrared image of a field of 256×256 pixels.

23. The method of claim 19 including recording about 128 to 1024 thermal images.

24. The method of claim 23 including recording the thermal images in a period of about 10 to 60 seconds.

25. The method of claim 19 including subdividing the predetermined area of skin into the plurality of subareas of about 24 to 100 square millimeters of skin based on a 256×256 pixel field.

26. The method of claim 19 including subdividing the predetermined area of skin into a plurality of subareas of about 4 to 16 pixels.

27. The method of claim 19 including analyzing the computed average temperature value of the selected subarea using a fast Fourier transform analysis.

28. The method of claim 19 including providing the presentation as a color-coded bitmap.

29. The method of claim 19 including subjecting the predetermined area of skin to either a cooling or warming air flow.

30. A method of detecting cancerous tissue, comprising the steps of:

a) recording a plurality of infrared images of a predetermined area of skin;

b) converting each of the plurality of infrared images into corresponding thermal images;

c) subdividing the predetermined area of skin into a plurality of subareas;

d) calculating an average temperature value and a temperature standard deviation for the plurality of thermal images of a selected one of the subareas, wherein the temperature standard deviation value for the selected subarea constitutes a time series for that subarea;

e) repeating the procedure of steps a) to d) on the remaining subareas of the predetermined area of the skin; and f) analyzing the temperature standard deviation value of the time series of each of the subareas, wherein when a spatial distribution of the temperature standard deviation value of a cluster comprising at least six congruent subareas is less than about 20% or more than 100% of the temperature standard deviation of the plurality of subareas, that cluster is determined to be cancerous.

31. The method of claim 30 including analyzing the temperature standard deviation value of each of the plurality of subareas to determine a contributing frequency of each temperature standard deviation value and displaying a presentation of the relative amplitude value of each frequency of the subareas, wherein when a spatial distribution of the amplitude of a given frequency of the cluster is less than about 25% or more than 100% of the average amplitude value of that frequency of the plurality of subareas, that cluster is determined to be cancerous.

32. A method of detecting cancerous tissue, comprising the steps of:

a) recording a plurality of infrared images of a predetermined area of skin;

b) converting each of the plurality of infrared images into corresponding thermal images;

c) subdividing the predetermined area of skin into a plurality of subareas;

d) calculating an average temperature value and a temperature for the plurality of thermal images of a selected one of the subareas, wherein the average temperature standard deviation value for the selected subarea constitutes a time series for that subarea;

e) repeating the procedure of steps a) to d) on the remaining subareas of the predetermined area of the skin;

f) analyzing the average temperature value of the time series of each of the subareas, wherein when a spatial distribution of the average temperature value of a cluster comprising at least six congruent subareas is less than about 20% or more than 100% of the average temperature of the plurality of subareas, that cluster is determined to be cancerous, and if a cluster is determined to be cancerous;

g) dividing the average temperature by the standard deviation of each of the subareas to derive a homogeneity of skin temperature (HST) value for each subarea, wherein the HST value for each subarea constitutes an HST time series for that subarea; and h) analyzing the HST value of the time series of each of the subareas, wherein when a spatial distribution of the HST value of a cluster comprising at least six congruent subareas is less than about 20% or more than 100% of the average HST value of the plurality of subareas, that cluster is determined to be cancerous.

* * * * *